United States Patent

Kotani et al.

Patent Number: 5,396,796
Date of Patent: Mar. 14, 1995

[54] HUMIDITY METER

[75] Inventors: Tsutomu Kotani; Shiro Nakagawa, both of Chiba, Japan

[73] Assignee: TDK Corporation, Tokyo, Japan

[21] Appl. No.: 260,098

[22] Filed: Jun. 15, 1994

Related U.S. Application Data

[63] Continuation of Ser. No. 61,661, May 13, 1993, abandoned.

[30] Foreign Application Priority Data

May 19, 1992 [JP] Japan ................ 4-039874 U

[51] Int. Cl.$^6$ ................ G01D 11/24; G01N 33/18
[52] U.S. Cl. ................ 73/431; 73/335.02
[58] Field of Search ........... 73/335.02, 335.03, 335.05, 73/29.02, 431; 422/104, 83; 206/305; 361/286; 324/664, 689, 694

[56] References Cited

U.S. PATENT DOCUMENTS

| | | | |
|---|---|---|---|
| 2,943,245 | 6/1960 | Ohlheiser | 73/335.02 X |
| 3,719,810 | 3/1973 | Ahlquist et al. | 73/29.02 X |
| 4,298,855 | 11/1981 | Mills | 338/35 |
| 4,399,404 | 8/1983 | Resh | 324/689 |
| 4,514,722 | 4/1985 | Batcheler et al. | 340/604 |
| 4,643,351 | 2/1987 | Fukamachi et al. | 73/335.02 X |
| 4,706,808 | 11/1987 | Guetersloh | 206/305 |
| 4,869,874 | 9/1989 | Falat | 73/335.05 X |
| 4,942,383 | 6/1990 | Lam et al. | 338/42 |
| 5,001,436 | 3/1991 | Scot et al. | 324/694 X |
| 5,012,360 | 4/1991 | Yamauchi et al. | 236/44 EX |
| 5,060,108 | 10/1991 | Baker et al. | 361/283 |
| 5,065,625 | 11/1991 | Nakagawa et al. | 73/336.5 |
| 5,195,358 | 3/1993 | Bleek et al. | 73/29.02 X |

FOREIGN PATENT DOCUMENTS

| | | |
|---|---|---|
| 0095180 | 11/1983 | European Pat. Off. . |
| 0183643 | 6/1986 | European Pat. Off. . |
| 58-015147 | 1/1983 | Japan . |

*Primary Examiner*—Robert J. Warden
*Assistant Examiner*—Robert Carpenter
*Attorney, Agent, or Firm*—Martin Novack

[57] ABSTRACT

A humidity meter has a housing (1) which has a separated sensor room (5) recessed in said housing (1) for securing a humidity sensor assembly (3). The humidity meter also has an electronic circuit (2) mounted on a printed circuit board (21) fixed in said housing (1), for processing humidity signal supplied by said humidity sensor assembly (3). Some examples of the process are analog-digital conversion of measured humidity signal, visible indication on a display screen, and/or interface with external circuit. Said humidity sensor assembly (3) is removably fixed on said printed circuit board (21) which doubles as a bottom wall (53) of said sensor room (5).

8 Claims, 4 Drawing Sheets

# HUMIDITY METER

This is a continuation of U.S. application Ser. No. 08/061,661, filed May 13, 1993, abandoned.

BACKGROUND OF THE INVENTION

The present invention relates to a humidity meter, in particular, relates to a humidity meter which has a humidity sensor with electrical impedance depending upon humidity, and an electronic circuit to process measured humidity signal.

A humidity meter of electrical impedance type is shown in U.S. Pat. No. 5,065,525, and U.S. patent application Ser. No. 07/986,688, assigned to the same assignee as the present application (EP patent application 92 310877.3).

A humidity meter of electrical impedance type must have two electronic circuits. A first circuit is to function to convert electrical impedance which depends upon humidity to electrical DC (direct current) potential which is the indication of measured humidity. A second circuit is to process said DC potential for various purposes. Some examples of the process are analog-to-digital conversion of DC potential of measured humidity in analog type to digital type signal, visible indication of converted digital signal, and/or interface for supplying the digital signal to an external circuit.

A first circuit is small and consumes less power, and therefore, it is assembled in a sensor assembly together with a sensor element itself. On the other hand, a second circuit is large, consumes much power thereby dissipates much heat.

When we try to mount a sensor element of above type and related electrical circuits in a single housing, the sensor element itself must be disposed in open air to measure humidity in open air, and must be isolated or separated completely in the housing from the electrical circuit which dissipates much heat so that the measured humidity is not affected by heat generated in the electrical circuit. If above conditions are not satisfied, accurate measurement of humidity would be impossible.

Simultaneously, the structure of humidity meter which satisfies above conditions must be simple.

A humidity meter which satisfies above conditions has not been known, although a humidity sensor element of impedance type, and electrical circuits for processing an output of a sensor element have been known.

SUMMARY OF THE INVENTION

It is an object of the present invention to overcome the disadvantages and limitations of a prior humidity meter by providing a new and improved humidity meter.

It is also an object of the present invention to provide a humidity meter which has a humidity sensor element and electronic circuits for processing electric signal of said sensor element in a single housing with no undesirable affection by heat generated in the electric circuits.

It is also an object of the present invention to provide a humidity meter which indicates measured humidity accurately.

The above and other objects are attained by a humidity meter comprising; a housing (1) having an inner space and a recessed sensor room (5) separated from said inner space, said sensor room (5) having an open window; a humidity sensor assembly (3) secured in said sensor room (5); an electronic circuit secured in said inner space and (2) mounted on a printed circuit board (21) fixed in said housing (1), for processing humidity signal supplied by said humidity sensor assembly (3); said sensor room (5) having a cylindrical wall (523) engaged with a frame (51) fixed around said window of said housing (1), and a bottom wall (53) which is a part of said printed circuit board (21), so that said sensor room (5) is separated from said 10 inner space of the housing (1); and said humidity sensor assembly (3) being fixed on said printed circuit board (21) through a plurality of conductive pins for electrical operation of the humidity sensor assembly (3) and related sockets fixed on said printed circuit board (21).

BRIEF DESCRIPTION OF THE DRAWINGS

The foregoing and other objects, features, and attendant advantages of the present invention will be appreciated as the same become better understood by means of the following description and the drawings wherein.

DESCRIPTION OF THE PREFERRED EMBODIMENTS

Figure 1:
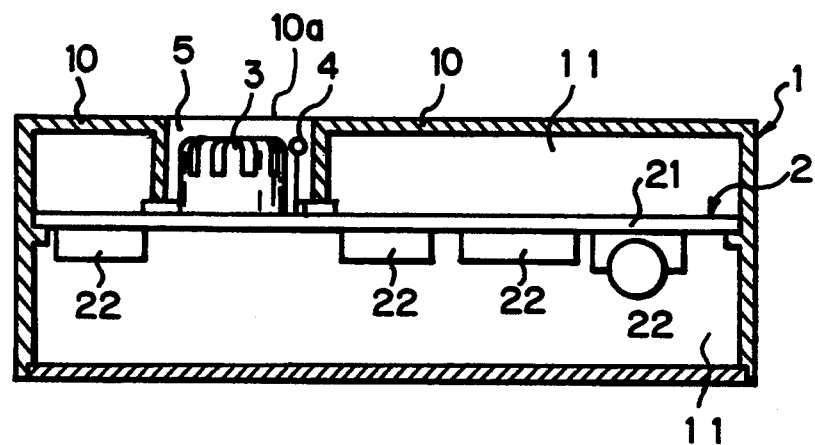
FIG. 1 shows cross sectional view of a humidity meter according to the present invention.
Figure 2A:
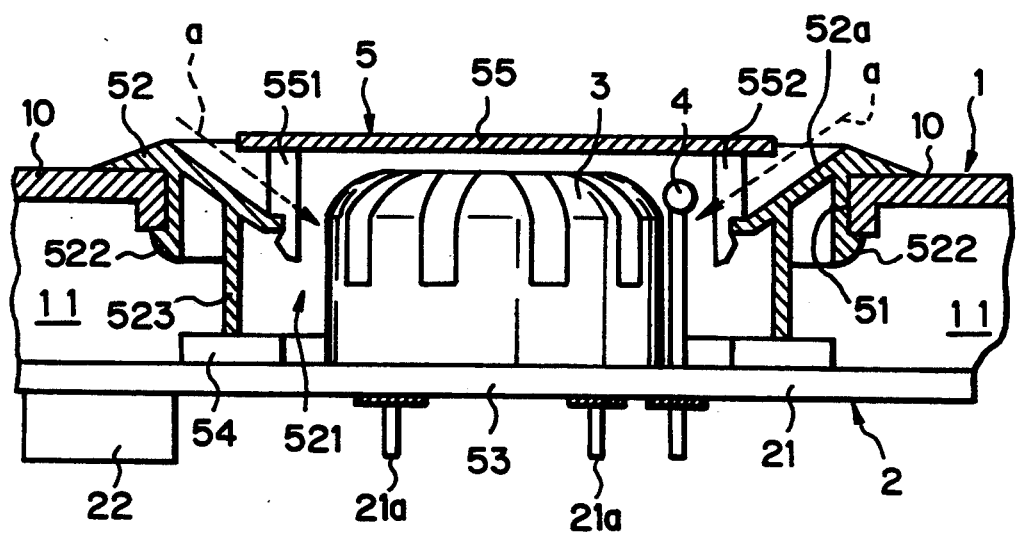
FIG. 2A shows a partially enlarged view of FIG. 1.
Figure 2B:
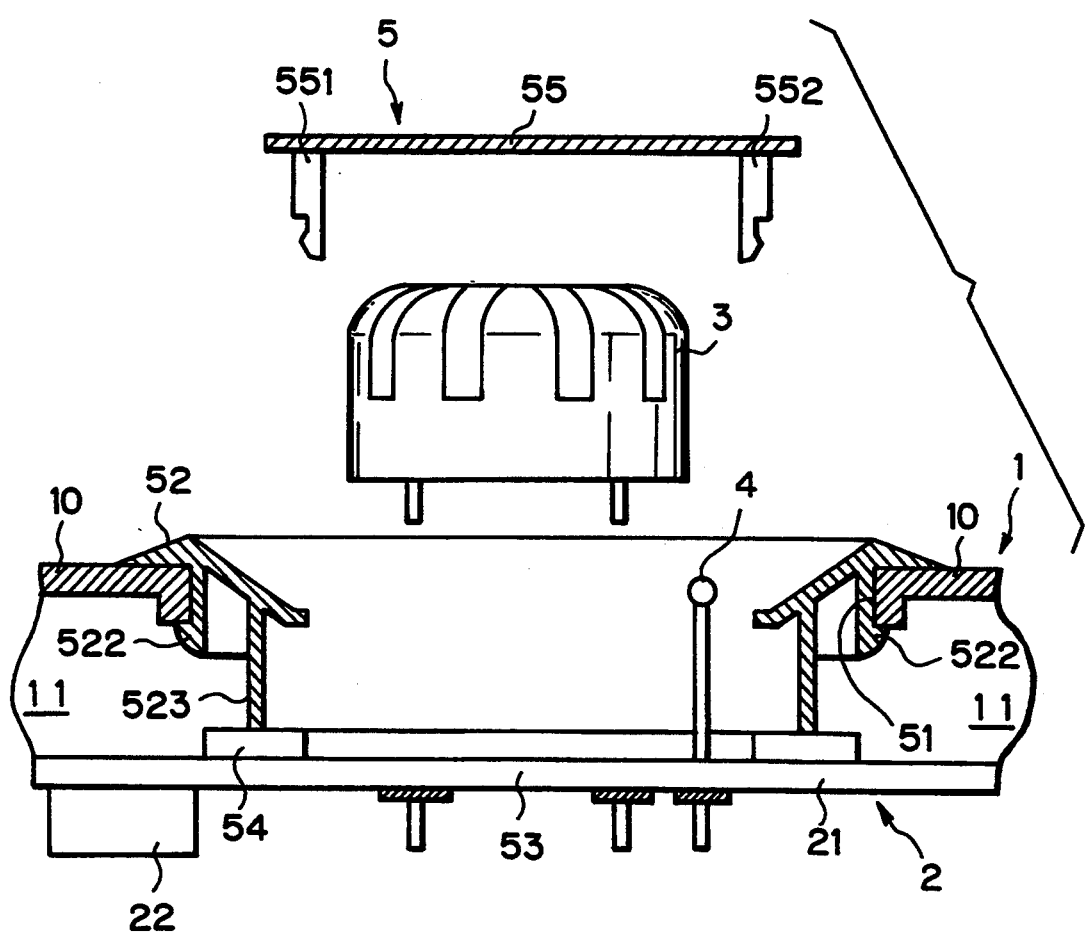
FIG. 2B is a separated view of FIG. 2A.

FIG. 1 shows a cross section of a humidity meter according to the present invention, FIG. 2A is an enlarged view of the main portion of FIG. 1, and FIG. 2B shows also an enlarged view of the main portion of FIG. 1 with a sensor assembly 3 and a cover 55 taken off.

Figure 3:
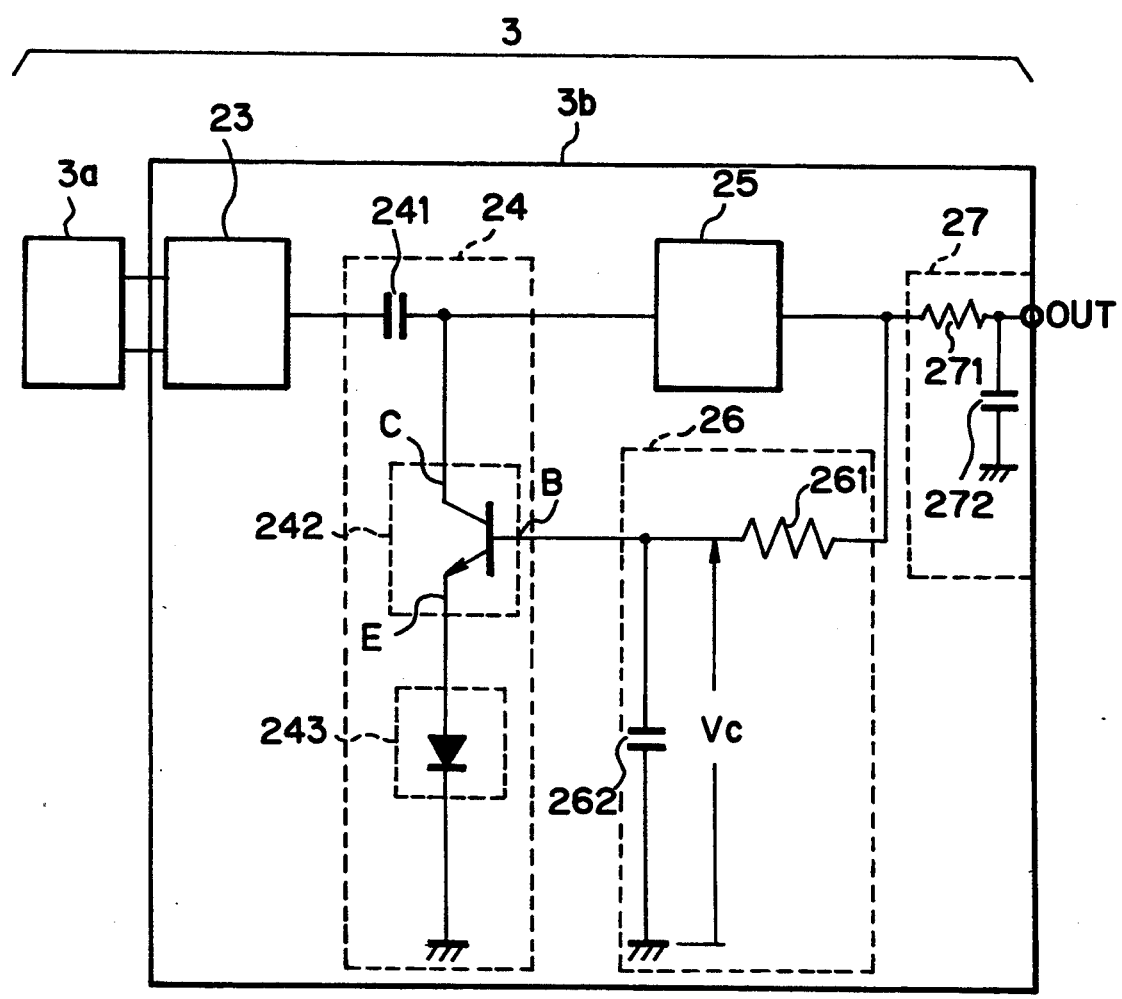
FIG. 3 is a circuit diagram of a humidity meter.
Figure 4:
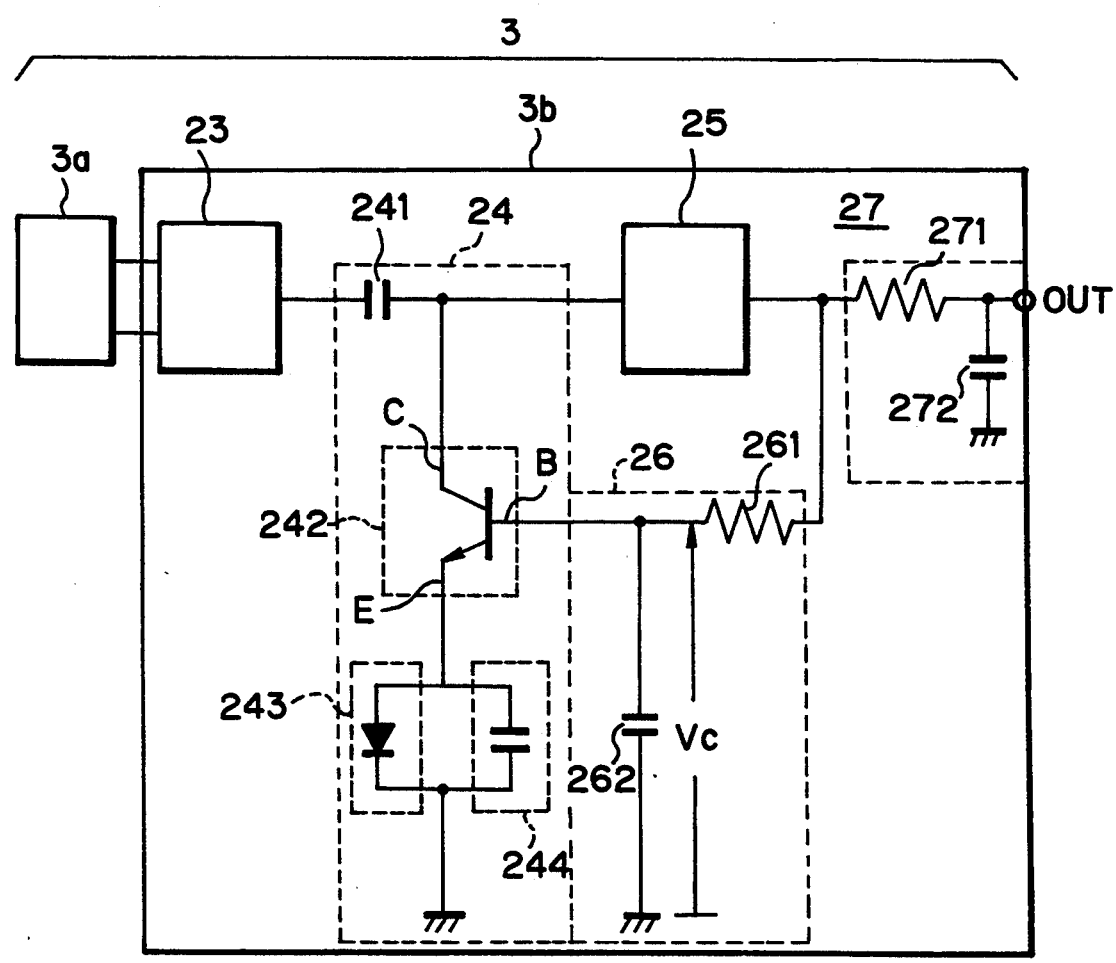
FIG. 4 is another circuit diagram of a humidity meter.

In the figures, the numeral 1 is a closed housing which has a recessed sensor room 5, 2 is an electronic device for processing output of the humidity sensor assembly, 3 is a humidity sensor assembly secured in the sensor room 5, 4 is a temperature sensor secured in the sensor room 5. The housing 1 is made of plastics having the inner space 11 which is separated from the sensor room 5. The humidity sensor assembly 3 includes a sensor element together with a first electronic circuit for operating the sensor element. The electronic device 2 has the second electronic circuit which includes, for instance, analog-to-digital conversion circuit for converting analog type output signal of the sensor assembly to digital type signal, an indication circuit for visual indication of measured humidity and/or temperature on an indication screen, an interface circuit for coupling measured humidity and/or temperature with an external circuit, et al. The first circuit for operating a humidity sensor element as shown in FIG. 3 or FIG. 4 is mounted in the sensor assembly 3.

The electronic device 2 has a circuit relating to measured humidity, and is mounted in the inner space 11 in the housing 1. The electronic device 2 has a printed circuit board 21 and circuit elements 22 mounted on the printed circuit board 21. In the embodiment, a temperature sensor 4 is also mounted on the printed circuit board 21, and therefore, the electronic device 2 includes also the circuit for processing measured temperature.

The humidity sensor assembly 3 is mounted in a sensor room 5 which is completely separated from the inner space 11 of the housing 1 so that the humidity sensor assembly 3 is disposed in open air. A sensor cover 55 is provided with snap fix with the housing 1 so that the humidity sensor assembly 3 and the temperature sensor 4 are secured under the cover 55, and some gap spacing are provided between the cover 55 and the housing 1 for air flow into the sensor room 5 as shown by the arrow (a).

The humidity sensor assembly 3 is removably mounted on the printed circuit board 21 through some conductive pins. In one embodiment, the number of pins is three, for a power supply line, an output line of measured humidity, and a ground line. Those pins function not only to supply electrical signals to the sensor assembly 3, but also to fix the sensor assembly on the printed circuit board 21 by holding those pins in a socket 21a fixed on the printed circuit board 21.

The sensor room 5 is essentially in rectangular shape provided in recessed space in the housing 1, which has an external wall 10 having an open window 10a for defining said sensor room 5. The external wall 10 has a flange 51 around said window 10a. The sensor room 5 is enclosed by an isolator 52 which has a rectangular essentially cylindrical wall 523 defining a cylindrical room 521, and being engaged with the flange 51 on the external wall 10. Preferably, the cylindrical wall 523 has a resilient ring-shaped projection 522 which has a recess for removably engaging with the flange 51 on the external wall 10. The sensor room 5 has a bottom wall 53, which is in the embodiment doubled by the printed circuit board 21. It is one of features of the present invention that the printed circuit board 21 for mounting electric elements doubles as a bottom wall of the sensor room for separating the sensor room from other inner space of the housing.

Preferably, a resilient seal member 54 is provided between the bottom wall 53 and the end of the cylindrical wall 523 for the whole peripheral length of the cylindrical wall 523, so that the sensor room 5 is sealed from the inner space 11 in the housing 10.

Preferably, the isolator 52 has a slope 52a on the cylindrical wall 523 so that said slope 52a goes down towards the center of the sensor room 5. The slope 52a facilitates air flow into the sensor room.

The cover 55 has a pair of arms 551 and 552, which engage removably with end of the slope 52a of the isolator 52. When the sensor assembly 3 is mounted and/or removed on/from the printed circuit board 21, the cover 55 is removed. Thus, the sensor assembly 3 is mounted and/or removed with simple operation. And, it should be noted that a sensor assembly is attached or removed to or from the apparatus without opening the housing, or without removing the printed circuit board from the housing.

FIG. 3 shows a circuit diagram of a humidity sensor assembly 3. The circuit of FIG. 3 is the improvement of the circuit shown in U.S. Pat. No. 5,065,625. In FIG. 3, the numeral 3a is a humidity sensor element which has electrical impedance depending upon ambient humidity. The impedance of the sensor element 3a changes exponentially in the range from $10^4 \Omega$ to $10^7 \Omega$ depending upon ambient humidity.

The numeral 3b shows a circuit which functions to provide DC output level indicating measured humidity depending upon impedance of the sensor element 3a. The circuit 3b has an impedance-frequency converter 23 which is essentially a generator providing frequency signal depending upon impedance of the sensor element 3a. The numeral 24 is a differentiation circuit which has adjustable time constant, the numeral 25 is a wave-form shaping circuit which provides an output pulse when an input level exceeds a predetermined reference level, and the numeral 26 is a feedback circuit which is implemented by an integration circuit to supply control voltage Vc from the output of the wave-form shaping circuit 25 to the differentiation circuit 24. The circuits 24, 25, and 26 function essentially as a pulse width modulation circuit which modulates pulse width of an output pulse of a generator 23 so that pulse width of an output of the wave-form shaping circuit 25 is wide when the frequency is low, and it is narrow when the frequency is high. The pulse width modulator compensates for exponential characteristics of the sensor element, and provides the linear output signal for the humidity.

The integrator 27 having a series resistor 271 and a capacitor 272 coupled between the output of the resistor 271 and the ground operates to provide DC level depending upon the frequency and the pulse width. The DC level of the output of the integrator 27 is linearly proportional to measured relative humidity.

The generator 23 provides the frequency which depends upon the humidity.

The output of the generator 23 is applied to the differentiation circuit 24, which has a series capacitor 241, and the resistance coupled between the output of the capacitor 241 and the ground. The resistance is variable, and is implemented by a series circuit of a transistor 242 and a diode 243. The impedance between a collector C and an emitter E of the transistor 242 is adjusted by control potential Vc applied to a base B of the transistor 242.

The diode 243 coupled between the transistor 242 and the ground improves the compensation of the linear relationship between the humidity and the output DC potential, in particular, when the humidity is low. A transistor has leak collector current $I_{CBO}$ even when a transistor is in OFF state. So, when a transistor is used as a variable impedance element it can not have impedance larger than a predetermined value. This causes an error of measured humidity. Further, said leak current $I_{CBO}$ depends upon ambient temperature, and causes the temperature dependency of a humidity meter. Further, temperature dependency of base potential for making a transistor OFF state may cause an error of measured humidity and/or temperature dependency of measured humidity. The diode 243 adds supplemental non-linear impedance in series to the impedance element 242 so that when the potential (or the humidity) is low the impedance is higher than that of the transistor 242. The supplemental impedance is implemented by voltage drop in forward direction of a semiconductor diode 243. A diode has large impedance when an input voltage is low in forward direction, but less impedance when an input voltage is high. Preferably, a diode 243 is a Shottky barrier diode.

The differentiated output of the differentiation circuit 24 is applied to the wave-form shaping circuit 25, which has a predetermined threshold level, and provides an output pulse during an input level of the wave-form shaping circuit exceeds said threshold level. Therefore, the pulse width of the output pulse of the wave-form shaping circuit 25 depends upon the frequency, in other words, the pulse width depends upon the humidity measured by the humidity sensor element 3a. The output of the wave-form shaping circuit 25 is applied to the integrator 27, which provides DC output signal which is linearly proportional to the humidity.

The output of the wave-form shaping circuit 25 is also applied to the base B of the transistor 242 through the integrator 26, which has the series resistor 261 and the capacitor 262 coupled between the output of the resistor 261 and the ground, for adjusting the time constant of the differentiation circuit 24.

In the above structure of the circuit, the exponential relations between humidity and impedance of a humidity sensor element 3a is compensated, and linear DC potential which is linearly proportional to humidity is obtained at the output terminal OUT.

FIG. 4 shows the modification of the circuit of FIG. 3, and the feature of the circuit of FIG. 4 is the presence of a capacitor 244 coupled parallel to the diode 243. As mentioned above, the presence of the diode 243 improves the linearity when humidity is low. However, since a diode has some voltage drop in forward direction when potential across the diode is higher than a predetermined value, that voltage drop causes an error in humidity when humidity is high. The capacitor 244 operates as a high-pass filter. As the voltage across the diode 243 is high the frequency applied to the diode 243 is also high. The capacitor 244 functions to reduce the voltage drop across the diode when humidity is high. Preferably, the capacitance of the capacitor 244 is in the range from 1000 pF to 0.1 μF, and still preferably, the capacitance is between 6800 pF and 8200 pF.

The circuit of FIG. 3 or FIG. 4 may have a thermister across the output terminal OUT and the ground for reducing the temperature dependency of measured humidity.

It should be appreciated that the sensor room 5 may include not only a humidity sensor assembly 3, but also a temperature sensor 4, and the printed circuit board 21 may mount a necessary circuit for processing an output of the temperature sensor. In that case, the present device may indicate both humidity and temperature, and/or transmit those measured values to external device, which is for instance a centralized data processing system.

As mentioned above in detail, the present humidity meter has a sensor room which is thermally separated from other circuits, and therefore, a sensor element is not influenced by heat dispersed by other circuits, and provides accurate measure of humidity.

From the foregoing it will now be apparent that a new and improved humidity meter has been found. It should be understood of course that the embodiments disclosed are merely illustrative and are not intended to limit the scope of the invention. Reference should be made to the appended claims, therefore, rather than the specification as indicating the scope of the invention.

What is claimed is:

1. A humidity meter comprising;
    a housing (1) having an inner space and a recessed sensor room (5) isolated from said inner space, said sensor room (5) having an open window,
    a humidity sensor assembly (3) secured in said sensor room (5),
    an electronic circuit (2) secured in said inner space and mounted on only one printed circuit board (21) fixed in said housing (1), for processing a humidity signal supplied by said humidity sensor assembly (3), said printed circuit board having a plurality of socket slots,
    said sensor room (5) having a cylindrical enclosing wall (523) engaged with a frame (51) fixed around said window of said housing (1), said cylindrical enclosing wall (523) circumferentially enclosing said sensor room (5), and a bottom wall (53) which is part of said printed circuit board (21), so that said sensor room (5) is completely isolated from said inner space of the housing (1), and
    said humidity sensor assembly (3) being fixed on said printed circuit board (21) by a plurality of conductive pins which pass through said slots, and are coupled with said electronic circuit.

2. A humidity meter according to claim 1, further comprising a resilient seal member (54) inserted between an end of said cylindrical wall (523) and said bottom wall (53) so that said sensor room (5) is sealed from said inner space of said housing (1).

3. A humidity meter according to claim 1, further comprising a circular cover (55) removably engaged with said cylindrical wall (523), an air flow gap between the cover (55) and the cylindrical wall (523) defining said open window.

4. A humidity meter according to claim 1, wherein said cylindrical wall (523) has a sloped top portion (52a) along the air flow gap into said sensor room.

5. A humidity meter according to claim 1, wherein a temperature sensor is secured in said sensor room, and is removably fixed on said printed circuit board (21).

6. A humidity meter according to claim 1, wherein said humidity sensor assembly (3) comprises a humidity sensor element (3a) which provides electrical impedance depending upon humidity, an impedance-frequency converter (23) which generates a frequency signal depending upon humidity, a differentiation circuit (24) having a variable time constant coupled with the output of said converter (23), a wave-form shaping circuit (25) coupled with the output of said differentiation circuit (24), an integration circuit (26) for feeding back the output of said wave-form shaping circuit (25) to a control input of said differentiation circuit (24), and another integration circuit (27) coupled with the output of said wave-form shaping circuit (25) to provide DC potential depending upon measured humidity at an output terminal.

7. A humidity meter according to claim 6, wherein said differentiation circuit (24) has a capacitor (241) and a variable resistor having a series circuit of a collector-emitter circuit having transistor and a diode, connected between one end of said capacitor and ground.

8. A humidity meter according to claim 7, wherein a second capacitor is coupled parallel to said diode.

* * * * *